US010111788B2

(12) United States Patent
Nishimura et al.

(10) Patent No.: US 10,111,788 B2
(45) Date of Patent: Oct. 30, 2018

(54) PACKAGE CONTAINING A PLURALITY OF WRAPPED ABSORBENT ARTICLES

(71) Applicant: UNICHARM CORPORATION, Shikokuchuo-shi, Ehime (JP)

(72) Inventors: Kiyoko Nishimura, Kanonji (JP); Yuki Noda, Kanonji (JP); Toshihisa Hayashi, Kanonji (JP); Taro Nittono, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 36 days.

(21) Appl. No.: 15/128,983

(22) PCT Filed: Mar. 23, 2015

(86) PCT No.: PCT/JP2015/058693
§ 371 (c)(1),
(2) Date: Sep. 25, 2016

(87) PCT Pub. No.: WO2015/146891
PCT Pub. Date: Oct. 1, 2015

(65) Prior Publication Data
US 2017/0105889 A1    Apr. 20, 2017

(30) Foreign Application Priority Data
Mar. 26, 2014  (JP) ................. 2014-064072

(51) Int. Cl.
*A61L 15/00*  (2006.01)
*A61F 13/551*  (2006.01)
(Continued)

(52) U.S. Cl.
CPC ........ *A61F 13/5514* (2013.01); *A61F 13/535* (2013.01); *A61F 13/55145* (2013.01);
(Continued)

(58) Field of Classification Search
CPC .......... A61F 13/5514; A61F 13/55145; B65D 75/38; B65D 85/16
(Continued)

(56) References Cited

U.S. PATENT DOCUMENTS 6,481,576 B1 * 11/2002 Watkins ............... A45C 11/008
190/109
8,197,455 B2 * 6/2012 Zander ................ A61F 13/5514
206/438
(Continued)

FOREIGN PATENT DOCUMENTS

JP  3018813 U   11/1995
JP  2002-37246 A  2/2002
(Continued)

OTHER PUBLICATIONS

Office Action in JP Application No. 2014-064072, dated Apr. 25, 2017.
(Continued)

*Primary Examiner* — Jacob K Ackun
*Assistant Examiner* — Jenine Pagan
(74) *Attorney, Agent, or Firm* — Hauptman Ham, LLP

(57) ABSTRACT

A package comprises: wrapped absorbent articles comprising: an absorbent article having an absorber; and a wrapper for individually wrapping the absorbent article, the absorbent article being placed on the wrapper and folded together with the wrapper, and the absorbent article being wrapped individually by the wrapper; and a bag containing the plurality of wrapped absorbent articles, wherein the wrapped absorbent articles are provided with a perfume, at least one surface of the bag comprises: aperture through which the perfume of the wrapped absorbent articles contained in the bag can pass; and a perfume indicator for indicating an existence of the perfume, a compressibility of the package is
(Continued)

10% or more when a load of 1.35 kg in weight is applied in an area of 100 mm×200 mm of the package for ten seconds, and a compression resilience of the package is 95% or more after ten seconds has passed after removal of the load.

8 Claims, 6 Drawing Sheets

(51) Int. Cl.
| | | |
|---|---|---|
| B65D 75/38 | (2006.01) | |
| B65D 75/58 | (2006.01) | |
| B65D 85/62 | (2006.01) | |
| B65D 75/54 | (2006.01) | |
| B65D 85/16 | (2006.01) | |
| A61F 13/84 | (2006.01) | |
| A61F 13/535 | (2006.01) | |
| A61F 13/56 | (2006.01) | |
| A61F 13/53 | (2006.01) | |

(52) U.S. Cl.
CPC ...... *A61F 13/5616* (2013.01); *A61F 13/8405* (2013.01); *B65D 75/38* (2013.01); *B65D 75/54* (2013.01); *B65D 75/5838* (2013.01); *B65D 85/16* (2013.01); *B65D 85/62* (2013.01); *A61F 2013/530007* (2013.01); *A61F 2013/8408* (2013.01); *B65D 2575/586* (2013.01)

(58) Field of Classification Search
USPC .......... 206/205, 210, 438, 440, 441, 459.5, 206/459.1, 457, 466, 497, 524.3, 494; 604/385.01, 358, 385.02
See application file for complete search history.

(56) References Cited

U.S. PATENT DOCUMENTS

| | | | | |
|---|---|---|---|---|
| 8,317,022 | B2 * | 11/2012 | Hagner | A61F 13/496 206/494 |
| 8,991,610 | B2 * | 3/2015 | Kuroda | A61F 13/5514 206/38 |
| 2002/0117419 | A1 * | 8/2002 | Tippey | A61F 13/5511 206/494 |
| 2003/0130632 | A1 * | 7/2003 | Costea | A61F 15/001 604/362 |
| 2007/0073255 | A1 * | 3/2007 | Thomas | A61F 13/551 604/385.02 |
| 2007/0142810 | A1 | 6/2007 | Visscher | |
| 2007/0144937 | A1 * | 6/2007 | Gilroy | A61F 13/551 206/776 |
| 2008/0011632 | A1 * | 1/2008 | Albino | A61F 13/5513 206/363 |
| 2009/0112174 | A1 * | 4/2009 | Drevik | A61F 13/5514 604/385.02 |
| 2010/0282637 | A1 * | 11/2010 | Clark, Jr. | B65D 75/46 206/581 |
| 2011/0216987 | A1 | 9/2011 | Hernandez et al. | |
| 2014/0224698 | A1 * | 8/2014 | Policicchio | B65D 85/16 206/494 |
| 2015/0136035 | A1 * | 5/2015 | Takahashi | A01K 1/0107 119/161 |

FOREIGN PATENT DOCUMENTS

| | | |
|---|---|---|
| JP | 2003-535650 A | 12/2003 |
| JP | 2005-118205 A | 5/2005 |
| JP | 2009-518158 A | 5/2009 |
| JP | 2011-20711 A | 2/2011 |
| WO | 2008/001332 A2 | 1/2008 |

OTHER PUBLICATIONS

Office Action in JP Application No. 2014-064072, dated Oct. 4, 2016.

International Search Report in PCT Application No. PCT/JP2015/058693, dated May 26, 2015.

Office Action in JP Application No. 2014-064072, dated Dec. 5, 2017, 4pp.

* cited by examiner

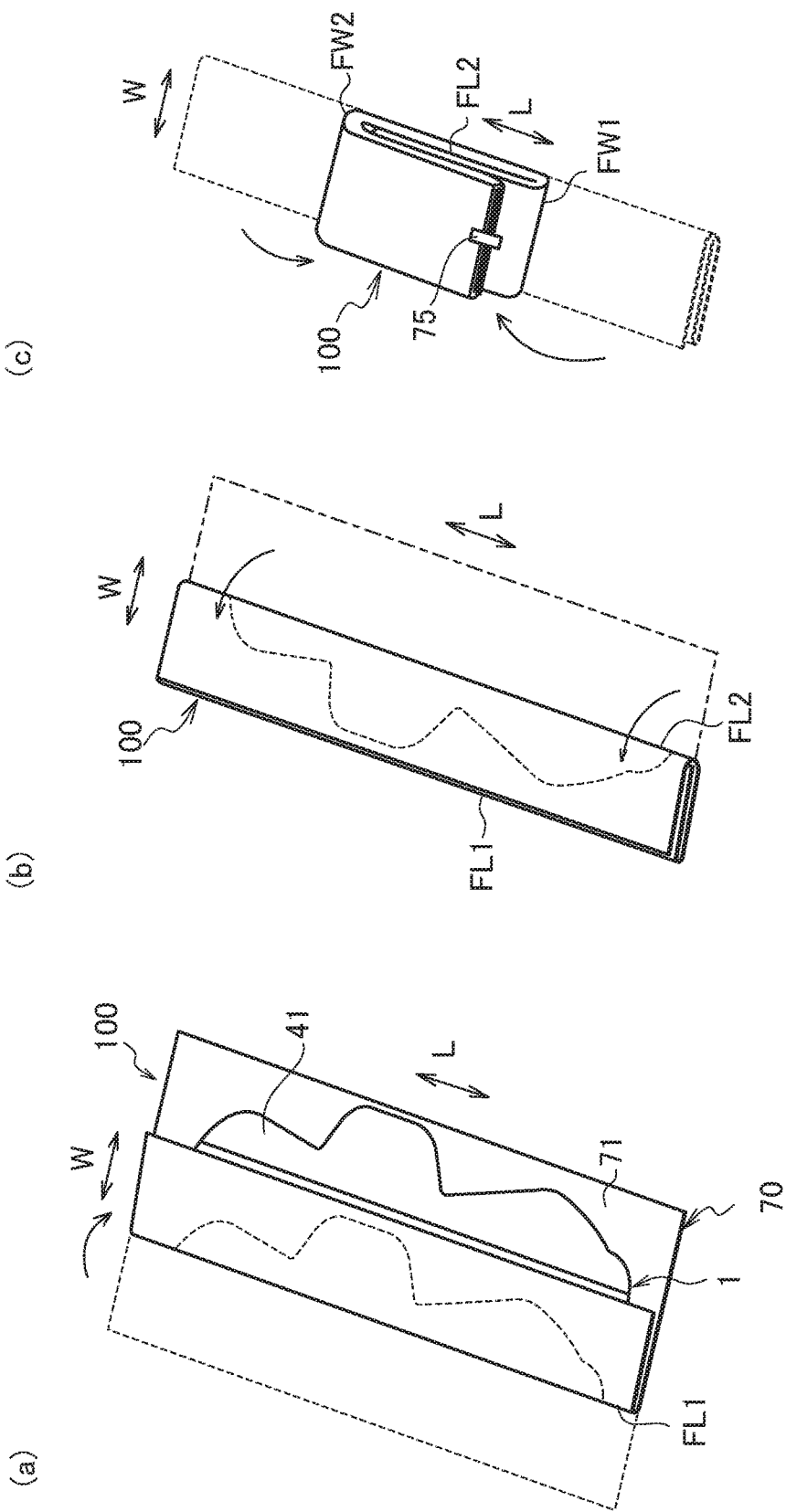

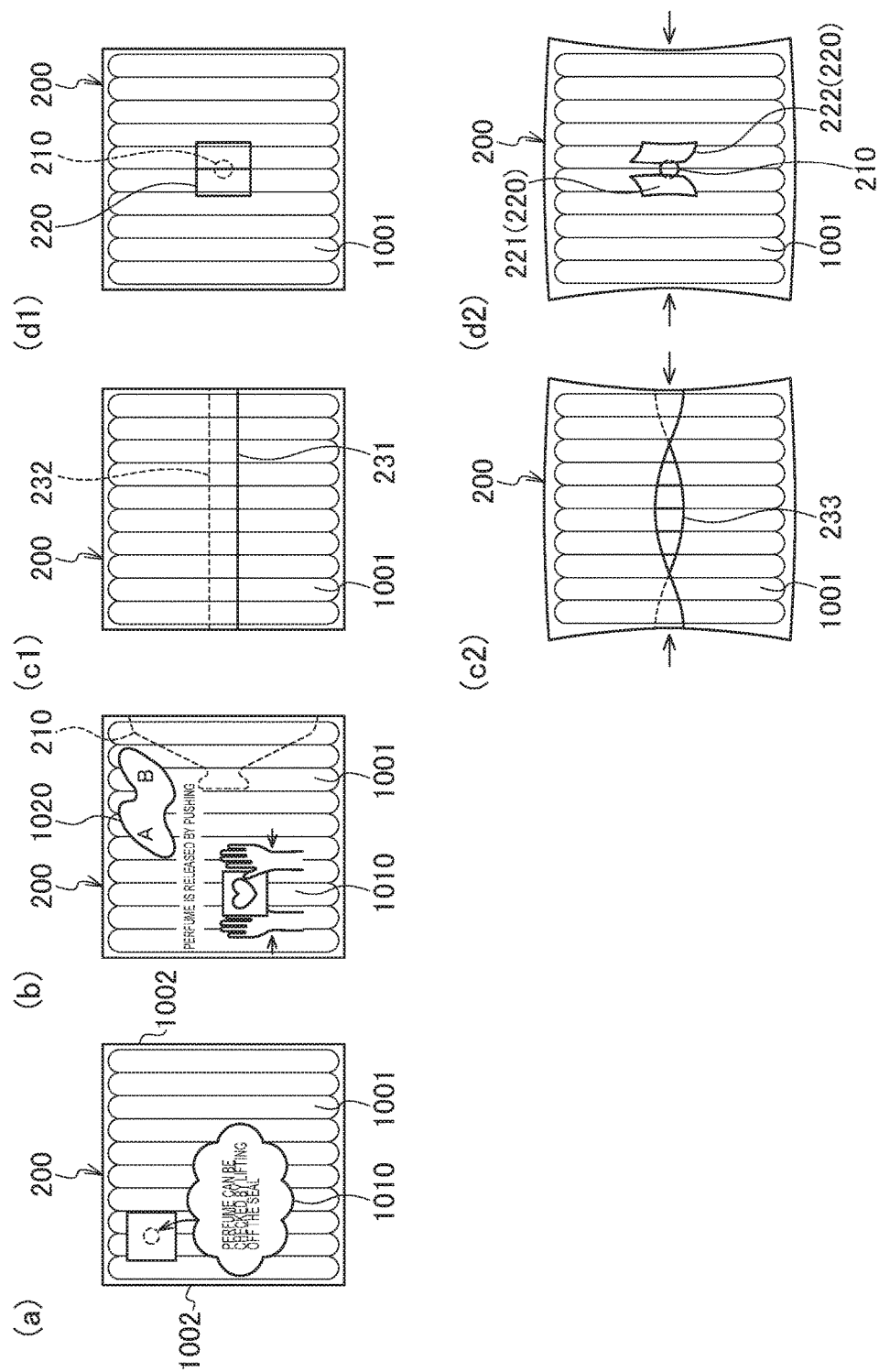

PACKAGE CONTAINING A PLURALITY OF WRAPPED ABSORBENT ARTICLES

RELATED APPLICATIONS

The present application is a national phase of International Application Number PCT/JP2015/058693, filed Mar. 23, 2015, which claims priority to Japanese Application Number 2014-064072, filed Mar. 26, 2014.

TECHNICAL FIELD

The present invention relates to a package containing absorbent articles individually wrapped by wrappers in the form of wrapped absorbent articles.

BACKGROUND ART

Scented absorbent articles have been known, such as pantiliners and sanitary napkins with floral fragrances or other fragrances (see Patent Literature 1, for example). An absorbent article in Patent Literature 1 is wrapped by a cellophane and film wrapper. A wrapped absorbent article is an absorbent article individually wrapped by a wrapper. A plurality of wrapped absorbent articles are enclosed in a package for marketing.

The scent of an absorbent article lasts through the user's wear of the absorbent article. Because an absorbent article will come into direct contact with the user's body, some users wish to know what kind of scent an absorbent article of interest is carrying. In particular, they wish to know what the scent is like before purchase or before opening the bag. Unfortunately, however, that has been difficult because wrapped absorbent articles are generally enclosed in sacks or bags which prevent users from checking the scent of the enclosed absorbent articles.

CITATION LIST

Patent Literature

Patent Literature 1: Japanese Utility Model No. 3018813

SUMMARY

In summary, a package according to the present disclosure includes: wrapped absorbent articles, comprising: an absorbent article having an absorber; and a wrapper for individually wrapping the absorbent article, the absorbent article being placed on the wrapper and folded together with the wrapper, and the absorbent article being wrapped individually by the wrapper; and a bag containing the wrapped absorbent articles, wherein the wrapped absorbent articles are provided with a perfume, at least one surface of the bag comprises: apertures through which the perfume of the wrapped absorbent articles contained in the bag can be pass; and a perfume indicator for indicating an existence of the perfume, a compressibility of the package is 10% or more when a load of 1.35 kg in weight is applied in an area of 100 mm×200 mm of the package for ten seconds, and a compression resilience of the package is 95% or more after ten seconds has passed after removal of the load.

BRIEF DESCRIPTION OF DRAWINGS

FIG. 5 is schematic perspective view of the wrapped absorbent article shown in FIG. 2, illustrating the steps of folding the wrapped absorbent article.

FIG. 6 shows packages according to modification examples.

DESCRIPTION OF EMBODIMENTS

(1) Configuration of Package

Figure 1:
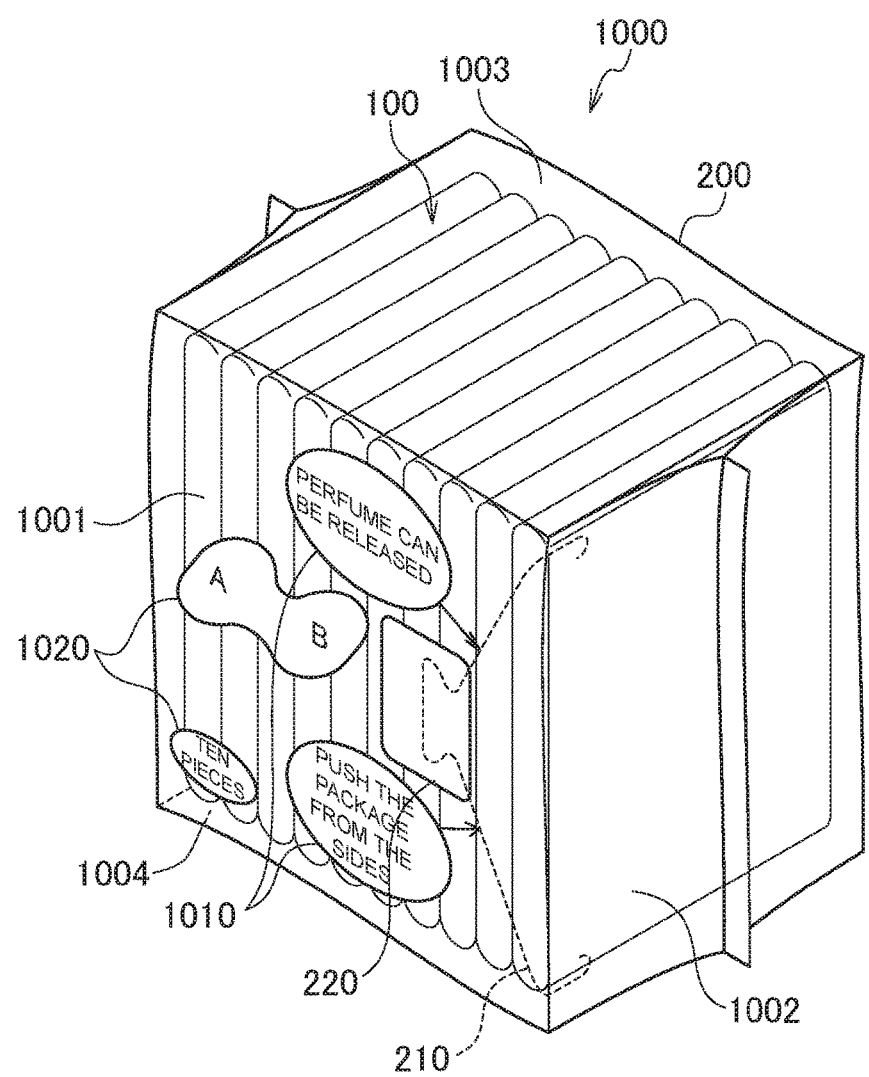
FIG. 1 is a perspective view of a package according to an embodiment.

A package according to embodiments will now be described with reference to FIGS. 1 to 5. FIG. 1 is a perspective view of a package. The package 1000 includes wrapped absorbent articles 100 and a bag 200 containing the plurality of wrapped absorbent articles 100.

Figure 2:
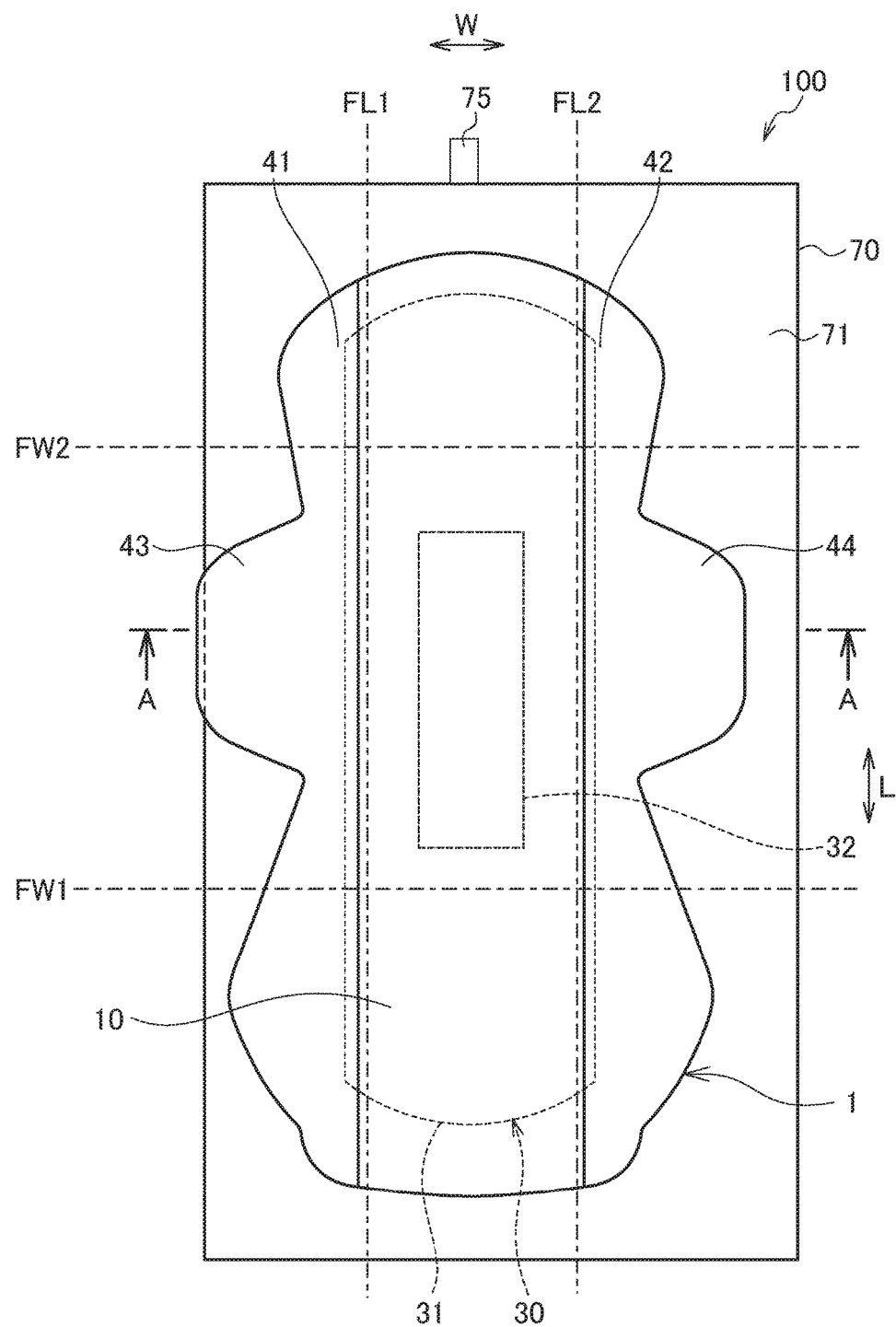
FIG. 2 is a plan view of a wrapped absorbent article according to an embodiment, seen from the skin-contacting side.
Figure 3:
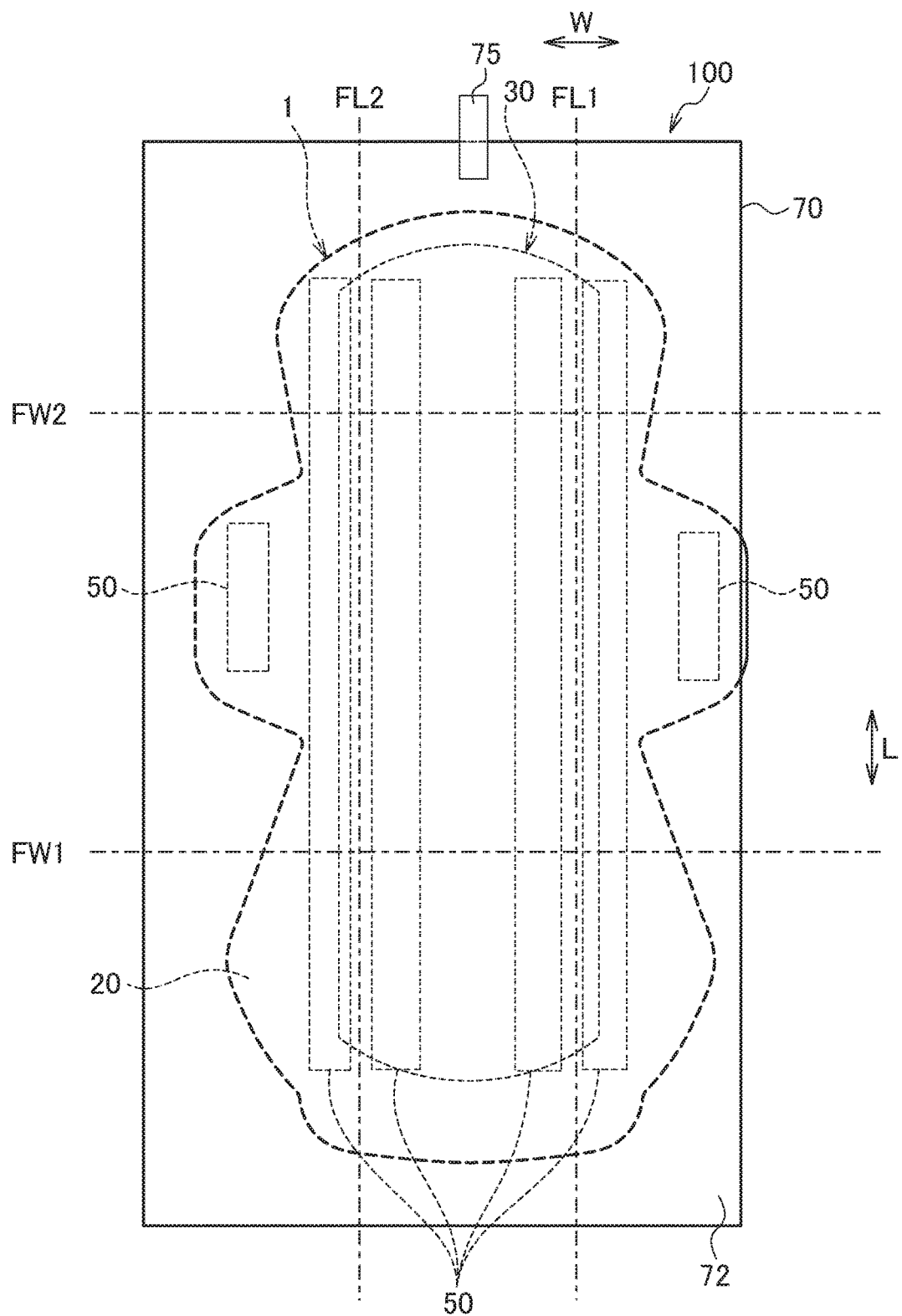
FIG. 3 is a back view of the wrapped absorbent article shown in FIG. 2, seen from the non-skin-contacting side.
Figure 4:
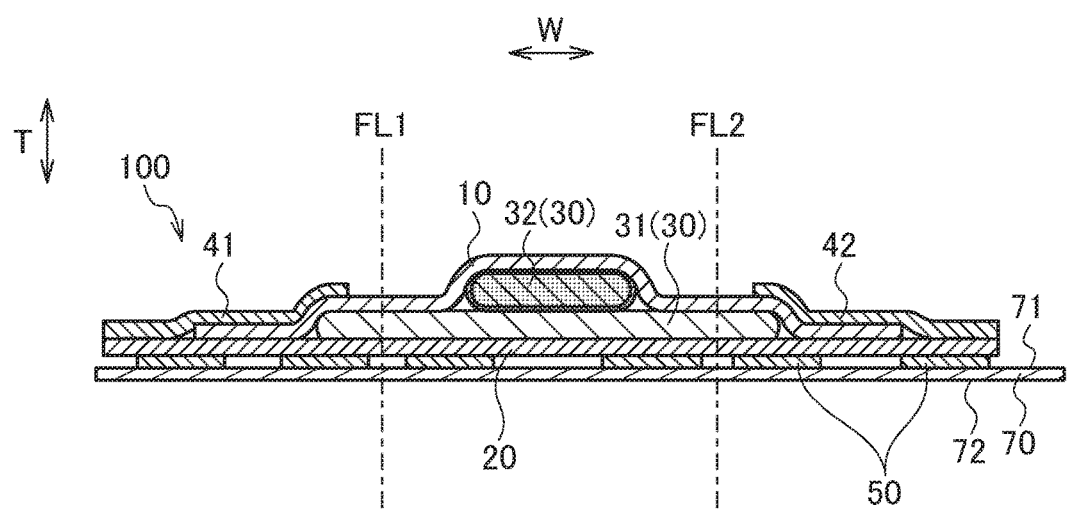
FIG. 4 is a cross-sectional view taken along the A-A in FIG. 2.

FIG. 2 is a plan view of a wrapped absorbent article; FIG. 3 is a back view of the wrapped absorbent article. FIG. 4 is a cross-sectional view taken along the A-A shown in FIG. 1. FIG. 5 is schematic perspective views of the wrapped absorbent article shown in FIG. 1, illustrating the steps of folding the wrapped absorbent article.

As shown in FIGS. 2 to 5, the wrapped absorbent article 100 has an absorbent article 1 and a wrapper 70 for individually wrapping the absorbent article 1. The absorbent article 1 according to the embodiment is, for example, a sanitary napkin.

First, the wrapped absorbent article 100 will be described. The absorbent article 1 is individually placed on the wrapper 70 and folded together with the wrapper 70 to make the wrapped absorbent article 100. FIGS. 2 and 3 show the developed absorbent article 1 and wrapper 70, after the wrapper 70 has wrapped the absorbent article 1 individually. The absorbent articles are individually wrapped by the wrappers in the form of the wrapped absorbent articles 100 and contained in a bag.

The absorbent article 1 includes a skin-contacting top sheet 10, a liquid-impermeable back sheet 20, and an absorber 30. The absorber 30 is provided between the top sheet 10 and the back sheet 20. Thus, the absorber 30 is shown in broken line in FIG. 2 and other figure. The absorber 30 is disposed at the center in the longitudinal direction L and the width direction W of the absorbent article 1. In the plan view of FIG. 2, the absorbent article 1 has the absorber 30, a main absorptive body extending along the longitudinal direction L, and wings 43, 44 disposed outward from the main absorptive body in the width direction W that is orthogonal to the longitudinal direction L. The absorbent article 1 further has side sheets 41, 42 disposed outward from the absorber 30 in the width direction W.

The top sheet 10 is permeable to liquid such as bodily fluid. The top sheet 10 covers at least a surface of the absorber 30. The top sheet 10 may be formed from any liquid-permeable material including, by way of example without limitation, non-woven fabric, woven fabric, porous plastic sheet, and mesh sheet. Materials for woven and non-woven fabric can include both natural and chemical fibers.

The top sheet 10 according to the embodiment can be formed from one or more materials. For example, it can be formed from woven fabric, non-woven fabric, polymeric film, film-nonwoven laminate, or combinations thereof.

The back sheet 20 is substantially equal to the top sheet 10 in length. The back sheet 20 can be formed from polymeric film, woven fabric, non-woven fabric, or combinations or composites thereof. A polymeric film can be formed from polyethylene, polypropylene, polyester, or combinations thereof. A polymer film can further be micro-embossed for printed design or message for consumers and/or at least partial coloring.

The absorber 30 contains hydrophilic fibers, pulp. The absorber 30 is formed of an absorbent bottom layer 31 and an absorbent top layer 32 on top of the absorbent bottom layer 31. The absorbent top layer 32 is smaller in size compared to the absorbent bottom layer 31 in both the longitudinal direction L and the width direction W. The absorbent bottom layer 31 and the absorbent top layer 32 may be integral or separately formed. The absorbent bottom layer 31 and the absorbent top layer 32 are glued to each other by a hot-melt adhesive.

The absorber 30 formed of the absorbent bottom layer 31 and the absorbent top layer 32 is made from a material(s) that is permeable to bodily fluid such as catamenial fluid. Examples of suitable materials for the absorber 30 can include cellulose, wood pulp fluff, rayon, cotton, and meltblown or coform polymers such as polyester and polypropylene.

The side sheets 41, 42 can be formed from a material(s) similar to that for the top sheet 10. In order for the side sheets 41, 42 to block leakage of catamenial fluid at lateral edge portions of the absorbent article 1, however, they are preferably hydrophilic or water-repellent. More specifically, spun-bond or SMS non-woven fabrics can be employed. Because the side sheets contact the wearer's skin, a non-woven air-through fabric is preferably used to form the side sheets because the fabric is less irritating to the skin.

The side sheets 41, 42 are disposed along the lateral sides of the top sheet 10. The side sheets 41, 42 cover the wings 43, 44 and part of the lateral edges of the absorber 30. In the absorbent article 1, peripheries of the top sheet 10, the side sheets 41, 42, and the back sheet 20 are joined to encase the absorber 30. The top sheet 10 and the back sheet 20 may be joined by using any one of or combination of heat-embossing, ultrasound welding, and gluing with hot-melt adhesive.

Adhesive 50 is applied on the back sheet 20 in some areas that come into contact with an undergarment (see FIG. 3). The adhesive 50 is applied either on the non-skin-contacting surface of the back sheet 20 or on the wrapper 70 that is a release liner and then transferred onto the non-skin-contacting surface of the back sheet 20. The areas of adhesive 50 are arranged in strips extending in the longitudinal direction L at the center in the width direction of the absorbent article.

The adhesive 50 is also disposed on undergarment-contacting surfaces of the wings 43, 44. Before using, the adhesive 50 is in contact with the wrapper 70, which protects the adhesive from going deteriorated. The wrapper 70 is removed by a user at the time of use. Another sheet of release paper may be used instead of the wrapper 70 to protect the adhesive from deterioration before the time of use. The adhesive can be, for example, a hot-melt adhesive.

The wrapper 70 wraps the absorbent article 1 individually. The wrapper 70 has an internal surface 71 facing the absorbent article 1 on the back sheet 20 side of the absorbent article 1, and an external surface 72, which does not face the absorbent article 1, located outside and containing the absorbent article 1.

A material(s) for the wrapper 70 can include, by way of example without limitation, films such as: plastic films made from polyethylene, polypropylene, polyester, or the like; nylon films; breathable drawn films containing barium sulfate fillers or the like; nonwoven-laminated films, and the like. Further, the internal surface of the wrapper 70 is treated so as to enable removal of the wrapper without reducing the capacity of the adhesive.

Folding of the wrapped absorbent article 100 will now be described. FIGS. 5(a) to 5(c) are schematic perspective views of the wrapped absorbent article 100, illustrating the steps of folding the wrapped absorbent article 100. The steps of folding the wrapped absorbent article 100 include an absorbent-article placing step, a first folding step, a second folding step, a joining step, and a third folding step.

In the absorbent-article placing step, the absorbent article 1 is placed on the wrapper 70. The wrapper 70 faces the back sheet 20 of the absorbent article 1. Here, the absorbent article 1 may be placed on the wrapper 70 sized for a single absorbent article 1, or a plurality of absorbent articles may be placed on a continuous wrapper on a conveyor at predetermined intervals. In this embodiment, for the convenience of the description, the folding is described by using a wrapper of the absorbent article which wraps a single absorbent article.

In the first folding step, as shown in FIG. 5(a), the wrapper 70 and the absorbent article 1 are folded on a first longitudinal fold line FL1 in the longitudinal direction L (see FIG. 2); a first lateral edge area including a first lateral edge of the absorbent article 1 is pulled internally in the width direction W over the first longitudinal fold line FL1. In the second folding step, as shown in FIG. 5(b), the wrapper 70 and the absorbent article 1 are folded on a second longitudinal fold line FL2 in the longitudinal direction L (see FIG. 2); a second lateral edge area including a second lateral edge of the absorbent article 1 is pulled internally in the width direction W over the second longitudinal fold line FL2.

In the next joining step, the lateral edge of the absorbent article 1 and the wrapper 70, which has been pulled internally in the width direction over the second longitudinal fold line FL2, is bonded to the wrapper 70 with a hot-melt adhesive. The hot-melt adhesive may be disposed so that a lateral edge of the internal surface 71 of the wrapper is bonded to the external surface 72 of the wrapper.

In this embodiment, the wrapper 70 is folded on the reference lines, the first longitudinal fold line FL1 and the second longitudinal fold line FL2, and then the lateral edge of the wrapper 70 is bonded with the hot-melt adhesive; however, the lateral edge need not be bonded. Otherwise, the lateral edge of the wrapper 70 may be bonded by thermal fusing, pressing, or ultrasonic welding.

In the third folding step, as shown in FIG. 5(c), the wrapper 70 and the absorbent article 1 are folded on a first widthwise fold line FW1 and a second widthwise fold line FW2 in the width direction W (see FIG. 2); end edge areas of the wrapper 70 and the absorbent article 1 are pulled internally in the longitudinal direction L of the absorbent article 1 over the first and second widthwise fold lines FW1 and FW2. By undergoing these steps, the wrapped absorbent article 100 is folded into a compact size.

Once the absorbent article 1 is folded as described above, one of the end edges in the longitudinal direction L of the wrapper 70 is fastened to the wrapper 70. The end edge of the wrapper 70 is fastened to an area in the wrapper 70 by an adhesive tape 75. The adhesive tape 75 is a single-layered polypropylene or polyethylene film or a multi-layered film in which different kinds of resin films are laminated.

When folding the wrapper 70 and the absorbent article 1 on the widthwise fold lines internally in the longitudinal direction L of the absorbent article 1, the end edge areas in the longitudinal direction L may be pulled one on top of another or may be adjoined with each other in the middle.

Folded in these ways, the wrapper 70 can wrap the absorbent article 1 individually in a compact size. Such a compact absorbent article 1 allows a user to carry it around conveniently because it does not occupy a large space in a bag such as a purse, a vanity bag, or the like. Further, a user can protect her privacy when she holds the absorbent article 1 in her hand, for example, on the way to a bathroom because the individually wrapped absorbent article 1 is compact enough to be enclosed in the user's hand so that the user does not need to go to the trouble of hiding or squeezing the absorbent article 1.

A perfume is applied to the internal surface of the wrapper. It is preferable that, in the package 100 according to the embodiment, the wrapping materials 2 are perfumed while the absorbent articles 1 are not perfumed.

There is no particular limitations for ingredients of a perfume and any known perfumes can be used without limitation; however, liquids containing perfume is preferred over particulates or powders bearing perfume because liquids are more easily impregnated in fibrous materials such as paper.

A perfume according to the embodiment has a floriental fruity fragrance which contains natural perfume ingredients such as mandarin, lemon, rose oil, geranium, vanilla, and ylang ylang.

Ingredients of the perfume may be those conventionally used in the technical field.

For example, the ingredients of the perfume that are highly volatile, having boiling points of about 250° C. or lower, or that are moderately volatile, having boiling points of about 250° C. to about 300° C., are preferably used.

Examples of highly volatile perfume ingredients can include, by way of example, anethole, benzaldehyde, benzyl acetate, benzyl alcohol, benzyl formate, iso-bornyl acetate, citronellal, citronellol, citronellyl acetate, para-cymene, decanal, dihydrolinalool, dihydromyrcenol, dimethyl phenyl carbinol, eucalyptol, 1-carvone, geranial, geraniol, geranyl acetate, geranyl nitrile, nerol, neryl acetate, nonyl acetate, linalool, linalyl acetate, phenyl ethyl alcohol, α-pinene, β-pinene, γ-pinene, α-ionone, β-ionone, γ-ionone, α-terpineol, β-terpineol, terpinyl acetate, and tentarome.

Examples of moderately volatile perfume ingredients can include, by way of example, amyl cinnamic aldehyde, dihydrojasmonic acid methyl, iso-amyl salicylate, β-caryophyllene, cedrene, cedryl methyl ether, cinnamic alcohol, coumarin, dimethyl benzyl carbinyl acetate, ethyl vanillin, eugenol, iso-eugenol, γ-methyl ionone, heliotropine, hexyl salicylate, cis-3-hexenyl salicylate, phenyl hexanol, vanillin, and veratraldehyde.

Besides the above-mentioned perfume ingredients, perfume compositions containing a perfume(s) with green-herbal aroma may also be used.

Here, a perfume refers to a simple perfume material as represented by group A and group B to be mentioned later. As used herein, a perfume composition includes a mixture of simple perfume materials or perfume materials such as natural essential oils or preparation bases formed from different perfumes, and includes those diluted or adjusted with solvent.

By employing a perfume composition containing a perfume with a green-herbal aroma, some discomforts associated with menses, especially psychological discomforts felt by a user will be safely and readily alleviated due to the action of the green-herbal aroma released from the perfume without oral administration or physical stimulation. In addition, a user would feel fresh.

A green-herbal aroma is a fragrance type and includes a green aroma (green note) and an herbal aroma (herbal note). A green aroma is a fragrance type that provides refreshing bouquet of freshly-cut grass and green leaves. An herbal aroma (herbal note) is a fragrance type that uses herbs and provides natural herbal bouquet.

A perfume composition containing a perfume with a green-herbal aroma preferably contains one or more perfumes selected from the group consisting of cis-3-hexenol, cis-3-hexenyl formate, cis-3-hexenyl acetate, cis-3-hexenyl propionate, cis-3-hexenyl butyrate, trans-2-hexenal, trans-2-hexenyl acetate, hexyl acetate, styrallyl acetate, 2-methyl-3-(3,4-methylenedioxyphenyl)-propanal (Helional, available from IFF), 3(4)-(5-ethylbicyclo [2,2,1]heptyl-2)-cyclohexanol, 2-pentyloxy glycolic acid allyl (allyl amyl glycolate, available from IFF), 4-methyl-3-decen-5-ol (Undecavertol, available from Givaudan), hexylaldehyde, 2,4-dimetyl-3-cyclohexenylcarboxyaldehyde (Triplal, available from IFF), and phenylacetaldehyde (hereinafter called "group A"). These perfumes can be commercially available. The perfumes in group A primarily provide green aromas.

In addition to the perfumes in group A, a perfume composition containing a perfume with a green-herbal aroma further preferably contains one or more perfumes selected from the group consisting of 1-menthol, 1,8-cineole, methyl salicylate, citronellal, camphor, borneol, isobornyl acetate, terpinyl acetate, eugenol, anethole, 4-methoxybenzyl alcohol, and estragole (hereinafter called "group B"). The perfumes in group B primarily provide herbal aromas.

The perfumes in group A preferably account for 0.5% to 30% by weight, more specifically 1% to 20% by weight in a perfume composition. The perfumes in group B preferably account for 1% to 30% by weight, more specifically 5% to 20% by weight in a perfume composition.

The perfumes in groups A and B are adjusted with, for example, an appropriate solvent to make a perfume composition. Solvents can include, by way of example, glycerol, propylene glycol, dipropylene glycol, iso-propyl myristate, triethyl citrate, 1,3-butylene glycol, polyethylene glycol, ethanol, and the like.

The amount of a perfume composition may be suitably selected for a purpose of psychologically positive effects depending on the size of the absorbent article 1, for example, between 0.3 mg and 100 mg, preferably between 0.3 mg and 20 mg, more preferably between 0.3 mg to 5 mg per absorbent article 1. The content of a perfume composition in these ranges is not too much or too strong yet still effective in alleviating discomforts felt by users.

The bag 200 will now be described. The bag 200 contains a plurality of wrapped absorbent articles 100.

The wrapped absorbent articles 100 contained in the bag 200 are stacked in a thickness direction T. More specifically, the wrapped absorbent articles 100 in the bag 200 are not arranged in the width or length direction of the absorbent article but are stacked in the thickness direction T alone.

The bag 200 may be configured to contain a plurality of wrapped absorbent articles, for example, a wicket bag as is in the embodiment or a flat bag. The bag according to the embodiment is made from polymeric resin film. Examples of materials for the bag can include polyethylene, polypropylene, or polyethylene terephthalate. The bag may be made from other material than the polymeric resin film as long as the material can provide the package with a compressibility of 10% or more and a compression resilience of 95% or more, which will be described later.

A perforated cut line has been formed in the bag 200. When the bag is torn along the perforated cut line, a window is formed in the bag to allow access to the wrapped absorbent articles. The perforated cut line provides apertures 210 through which the perfume of the wrapped absorbent articles contained in the bag can pass. An openable and closeable opening for the window is made in the bag by the tearing along the perforated cut line. A sealing member 220 is disposed at a peripheral part of the opening. The sealing member 220 is removable from and re-attachable to the bag surface. Thus, a user can lift off the opening of the bag to gain access to the wrapped absorbent articles through the window and close the window by lifting down the opening.

The package 1000 with the above configuration will now be described. The package 1000 has a substantially rectangular parallelepiped shape, at least having a front surface 1001 located in the front in FIG. 1, a pair of side surfaces 1002 located on either side of the front surface, a top surface 1003 located at top in FIG. 1, and a bottom surface 1004 located at bottom in FIG. 1.

In store settings, the package is displayed so that the front surface 1001 is seen from customers. For example, the product name, logo, and the number of the items (e.g., pads) are shown on the front surface. In the embodiment, product information 1020 including the product name and logo of the absorbent articles and the number of the contained absorbent articles is provided on the front surface of the package. The product information 1020 may be provided in one area or in a plurality of areas.

Perfume indicator 1010 is provided on the front surface of the package to indicate an existence of the perfume. The perfume indicator indicates that the wrapped absorbent articles are scented, that users can check the scent through the bag, and how to check the scent. The perfume indicator 1010 may be provided in one area, or in a plurality of area.

A compressibility of the package 1000 is 10% or more when the package 1000 is pressed by a load of 1.35 kg in weight in an area of 100 mm×200 mm for ten seconds. A compression resilience of the package 1000 is 95% or more after ten seconds after removal of the load.

A compressibility of the package is the rate of change in length when the package is pressed down in a state that the wrapped absorbent articles is enclosed in the bag. The compressibility can be calculated as follows. First, the package is mounted on a flat metallic table so that one of a pair of opposite surfaces (e.g., the pair of side surfaces) of the package abuts against the table. Then the distance between the surface abutting against the table and other surface among the pair of opposite surfaces (e.g., the pair of side surfaces) is measured. The measured distance is defined as a pre-compression thickness of the package.

Next, a metallic plate having an area of 100 mm×200 mm is placed on the other surface among the pair of opposite surfaces (e.g., the pair of side surfaces) of the package. The metallic plate is 5 mm in thickness and 1.35 kg in weight. The load of 1.35-kg is applied to the package. After the metallic plate is mounted on the package for ten seconds, the distance between the surface abutting the metallic plate and the surface abutting the table are measured. This distance is defined as a post-compression thickness of the package. The compressibility can be calculated by the following expression:

Compressibility (%)=(package's pre-compression thickness−package's post-compression thickness)/package's pre-compression thickness×100

A compression resilience of the package is the rate of change in length after ten seconds after removal of the metallic plate from the package. The compression resilience can be calculated as follows. The post-compression thickness of the package measured above is now defined as a pre-resilience thickness of the package. The metallic plate (i.e., the load of 1.35 kg) is removed from the package, and ten seconds later, the distance between the surface abutting against the table and the other surface is measured. This distance is defined as a post-resilience thickness of the package. The compression resilience can be calculated by the following expression.

Compression resilience (%)=package's post-resilience thickness/package's pre-resilience thickness×100

The weight of the metallic plate is intended to resemble a situation where a user pushes the side surfaces of the package with hands. Multiple package samples were pushed and compressed with hands, and loads applied for the compressions were measured. An average load of the multiple samples was calculated. The size of the metallic plate, 100 mm×200 mm, is intended to resemble a hand of a user.

The package according to the embodiment has a substantially rectangular parallelepiped shape, having three pairs of opposite surfaces. It is preferable that at least one of the three pairs has the compressibility and compression resilience as described above upon compression.

Next, how to check the scent of the package with the above configuration will be described. Messages for users such as "Perfume can be released" and "Push the package from the sides" as the perfume indicator are provided on the front surface of the package. A user contemplating purchase of the package will take the package from the shelf, and hold the package on the sides and laterally pushes the package, urged by the message "Push the package from the sides".

As the user pushes the package, air in the bag exits to the outside through the apertures 210 of the perforated cut line. The perfume indicator includes an arrow to indicate that the perfume is released through the perforated cut line. Being informed that the perfume is available around the perforated cut line, a user can check the perfume.

When the user releases the package, the package returns to its original shape with the compression resilience of 95% or more. Hence, when another user wishes to check the scent of the same package, the package can go through the compression and resilience again.

(2) Functions and Benefits

According to the package with the above configuration, a user can check the scent carried by the wrapped absorbent articles prior to purchase or before opening the bag. Thus, the user can decide whether she would like to purchase the product or not after checking the scent.

Looking at the perfume indicator, a user will realize that the product is scented and know how to check the scent, so that she can reliably check the scent if she wishes to do so.

Because the compressibility of the package is 10% or more, air inside the package may be released to the outside when the package is externally pushed and thereby collapsed. Because a compression resilience of the package is 95% or more, the collapsed package can return to its original product shape. Because the package can return to its original shape from the collapsed shape, the package can be compressed repeatedly to check the scent.

The perfume indicator and the perforated cut line in the form of the apertures 210 are disposed on the same surface (the front surface) of the package. Therefore, a user can look at the perfume indicator and check the scent at the same time.

A surface of the package is opposed to sides of the wrappers that wrap the absorbent articles. When a user holds the package and tries to push the package while looking at the front surface, she would typically compress the package on the side surfaces. Because the wrapped absorbent articles are stacked in this compressive direction, gaps between the wrapped absorbent articles are closed upon the compression, making it easy for the user to compress the entire package.

In store settings, a product is usually displayed so that the front surface thereof is seen from users. Because the perfume indicator and apertures are disposed on the front surface of the package, a user will notice that the product on the shelf is scented.

The apertures 210 form the perforated cut line for breaking the bag. When the bag is torn along the perforated cut line, the window is formed in the bag to provide access to the wrapped absorbent articles. The apertures can release the scent therethrough before the bag is opened, and can define the window after the bag is opened. This configuration is simpler compared to a configuration having an aperture(s) and a perforated cut line separately.

The bag is made from polymeric resin film. The bag made from polymeric resin film is easily deformed when pushed by a user and also easily returns to its original shape.

(3) Other Embodiments

Packages according to modification examples will now be described with reference to FIGS. 6(*a*) to 6(*d*2). FIGS. 6(*a*) to 6(*d*2) are front views of packages according to modification examples 1 to 4. In the description of the modification examples, like configurations as the above embodiment will be given like reference signs and will not be illustrated in detail.

FIG. 6(*a*) illustrates the package according to the modification example 1. A round aperture is formed in the front surface of the package. The package has a sealing member 220 covering the aperture. The sealing member 220 is attached to a surface of a bag. When a user removes the sealing member 220, the aperture 210 is exposed. The user can check the scent of wrapped absorbent articles by removing the sealing member 220. The sealing member 220 is re-attachable to the bag even though it was once removed. Thus, a user can open and close the aperture 210 repeatedly. Perfume indicator 2010 instructs that the user can check the scent by lifting off the sealing member 220. The sealing portion keeps the aperture closed except when a user checks the scent, preventing the scent from escaping through the aperture, and keeping the package interior clean.

FIG. 6(*b*) shows the package according to the modification example 2. Perfume indicator on the package according to the modification example 2 includes text and picture to instruct that the user can check the scent by pushing the package. Alternatively, the perfume indicator may be formed by either one of text and picture.

FIGS. 6(*c*1) and 6(*c*2) show the package according to the modification example 3. FIG. 6(*c*1) shows a state in which the package has not been compressed, while FIG. 6(*c*2) shows a state in which the package has been compressed. The front surface of a bag is formed of two sheets. The two sheets 231, 232 are partially overlapped. At least part of the overlapped portion of the sheets is not joined so that the overlapped portion opens when the package is compressed.

More specifically, the two sheets includes the first sheet 231 extending from the side of a top surface toward the side of a bottom surface and the second sheet 232 extending from side of the bottom surface toward the side of the top surface. A lower end of the first sheet 231 overlaps an upper end of the second sheet 232. The first and second sheets are not joined together where the lower end of the first sheet 231 overlaps the upper end of the second sheet 232.

When a user compresses the package on the side surfaces, the lower end of the first sheet and the upper end of the second sheet are flexed, creating a gap 233 between the first and second sheets. FIG. 6 (*c*2) shows the state in which the package has been compressed. The scent of the wrapped absorbent articles escapes from the bag through the gap. When the user releases the side surfaces of the package, the flex of the first and second sheets is straightened so that the package returns to the state shown in FIG. 6 (*c*1).

FIGS. 6 (*d*1) and 6 (*d*2) show the package according to the modification example 4. FIG. 6 (*d*1) shows a state in which the package has not been compressed yet, while FIG. 6 (*d*2) shows a state in which the package has been compressed.

The package has a sealing member 220 covering an aperture. The sealing member 220 is attached to a surface of a bag. The sealing member 220 has a first sealing member 221 and a second sealing member 222 positioned side by side. One half of the aperture 210 is covered by the first sealing member 221 while the other half of the aperture 210 is covered by the second sealing member 222.

A laterally external end of the first sealing member 221 and a laterally external end of the second sealing member 222 are unreleasably bonded to the bag. On the other hand, a laterally internal end of the first sealing member 221 and a laterally internal end of the second sealing member 222 are releasably bonded to the bag.

When the package is pushed by a user on the side surfaces, the laterally internal end of the first sealing member 221 swings up with respect to the laterally external end of the first sealing member 221, while the laterally internal end of the second sealing member 222 swings up with respect to the laterally external end of the second sealing member 222. In this way, the aperture 210 of the package is exposed. FIG. 6(*d*2) shows the state in which the package has been compressed. The scent of the wrapped absorbent articles escapes from the bag through the aperture 210. When the user releases the side surfaces of the package and re-attaches the sealing members to the bag surface, the package returns to the state shown in FIG. 6(*d*1).

Hence, the present invention can be practiced through modifications and variations without departing from the contemplated scope and spirit as defined by the claims. Thus, the description in this specification is intended for illustration only and does not limit the present invention in any way.

For example, the absorbent articles contained in the package are not limited to sanitary napkins, but they may be other absorbent articles such as pantiliners, disposable diapers or incontinence pads, etc.

Further, the shape of an aperture is not limited to a dot-like shape, but it may be a heart or diamond shape or a flower or animal pattern. For an embodiment with a sealing portion, perfume indicator may be provided on the sealing portion. Furthermore, the apertures may be disposed in the perfume indicator. If the apertures are disposed this way, the scent is released at a position closer to the pertaining information. This will help the user check the scent with more ease.

The present application incorporates by reference the entirety of Japanese Patent Application Number 2014-064072, filed Mar. 26, 2014.

INDUSTRIAL APPLICABILITY

A package containing wrapped absorbent articles in a bag, enabling a user to check a scent of the absorbent articles through the bag before opening the bag, can be provided.

The invention claimed is:

1. A package comprising:
wrapped absorbent articles comprising: an absorbent article having an absorber; and a wrapper for individually wrapping the absorbent article, the absorbent article being placed on the wrapper and folded together with the wrapper, and the absorbent article being wrapped individually by the wrapper; and
a bag containing the plurality of wrapped absorbent articles, wherein
the wrapped absorbent articles are provided with a perfume,
at least one surface of the bag comprises: aperture through which the perfume of the wrapped absorbent articles contained in the bag can pass; and a perfume indicator for indicating an existence of the perfume,
a compressibility of the package is 10% or more when a load of 1.35 kg in weight is applied in an area of 100 mm×200 mm of the package for ten seconds, and
a compression resilience of the package is 95% or more after ten seconds has passed after removal of the load.

2. The package according to claim 1, wherein the wrapped absorbent articles are stacked in a thickness direction of the absorbent articles, and
the surface of the package faces a side part of the wrappers that wrap the absorbent articles.

3. The package according to claim 1, wherein the surface is a front surface of the package.

4. The package according to claim 1, wherein the aperture is disposed in the perfume indicator.

5. The package according to claim 1, further comprising a sealing portion covering the aperture and removably fastened to a surface of the bag, wherein
the sealing portion is re-attachable to the bag after the sealing portion is removed from the bag.

6. The package according to claim 5, wherein the perfume indicator is disposed on the sealing portion.

7. The package according to claim 1, wherein the aperture form a perforated cut line for tearing the bag, and
when the bag is torn along the perforated cut line, a window is made in the bag to access to the wrapped absorbent articles.

8. The package according to claim 1, wherein the bag is made from polymeric resin film.

* * * * *